(12) United States Patent
Liao

(10) Patent No.: US 6,436,075 B1
(45) Date of Patent: Aug. 20, 2002

(54) SYRINGE

(76) Inventor: Hsueh-Cheng Liao, No. 8-3, Lane 135, Chungcheng Rd., Taichung (TW)

( * ) Notice: Subject to any disclaimer, the term of this patent is extended or adjusted under 35 U.S.C. 154(b) by 139 days.

(21) Appl. No.: 09/691,444

(22) Filed: Oct. 18, 2000

(51) Int. Cl.[7] .................................................. A61M 5/00
(52) U.S. Cl. ........................................ 604/181; 604/192
(58) Field of Search ................................ 604/110, 195, 604/192, 198, 197, 241, 243, 181

(56) References Cited

U.S. PATENT DOCUMENTS 4,718,463 A * 1/1988 Jurgens et al. .......... 134/169 R
5,616,135 A * 4/1997 Thorne et al. .............. 604/192

* cited by examiner

Primary Examiner—Edward K. Look
Assistant Examiner—Kimya N McCoy
(74) Attorney, Agent, or Firm—Pearne & Gordon LLP

(57) ABSTRACT

A syringe includes a hollow barrel adapted to be pre-filled with medicine. A piston is movably received in an open end of the hollow barrel and the open end is closed by a first seal. A closed end of the barrel has a stub extending out therefrom and a through hole is centrally defined in the stub. A second seal is formed on the top of the stub to close the through hole. An annular groove is defined in the closed end of the hollow barrel and surrounds the stub. A needle breaks through the second seal when the needle hub is attached to the stub. Further, the stub can be separated from and then received in the hollow barrel after the syringe has been used.

6 Claims, 5 Drawing Sheets

SYRINGE

BACKGROUND OF THE INVENTION

1. Field of the Invention

The present invention relates to a syringe, and more particularly to a combination syringe and ampoule to decrease the volume of medical garbage, and to simplify conventional vaccination procedures.

2. Description of Related Art

A conventional syringe is hollow and has to be filled with a vaccine etc so that a patient can be treated. The vaccine has to be kept in a sealed vessel such as an ampoule, so the purity of the vaccine can be maintained. One type of commonly used ampoule is shown in FIG. 5, and has a main body, a top and a neck extending between the neck and the top. To access the vaccine, the ampoule is broken at the neck and a needle of the syringe is inserted into the vaccine and then the vaccine is extracted from the ampoule by a plunger of the syringe being pulled back. However, this operation has at least two disadvantages which are as follow:

1. There are several steps in accessing the vaccine and treating the patient, which are at best inconvenient, and at worst, dangerous. For example, the breaking of the neck of the ampoule may lead to cutting a medic which is bad enough in itself, but with the possibility of transmissible diseases through exposure to blood, the result could be fatal. Then, the extraction of the vaccine etc from the ampoule is prone to spillage and even contamination.

2. The costs in use of equipment and to the environment are very high. The volume of the garbage is large because the ampoule and the syringe are both discarded. Furthermore, the health authority has to face high costs in the correct disposal of medical waste, and if that waste has an unnecessarily high volume due to so many used ampoules, then the costs will be accordingly high.

The present invention has arisen to mitigate and/or obviate the disadvantages of the conventional syringe.

SUMMARY OF THE INVENTION

In accordance with one aspect of the present invention, a syringe includes a hollow barrel pre-filled with medicine. A piston is movably received in an open end of the hollow barrel and the open end of the hollow barrel is closed by a first seal adhered thereon. Another end of the hollow barrel is closed and has a stub extending out therefrom and a through hole is centrally defined in the stub. A second seal is formed on a top of the stub to close the through hole. An annular groove is defined in the closed end of the hollow barrel and surrounds the stub. Whereby, in use a needle breaks through the second seal when the needle hub is attached to the stub, a plunger is attached to the piston and in doing so the first seal is broken, and the syringe is ready for treatment of a patient. Further, the stub can be separated from the barrel and received in the hollow barrel after use, whereby the syringe is very safe for post-use handling and disposal.

Further benefits and advantages of the present invention will become apparent after a careful reading of the detailed description with appropriate reference to the accompanying drawings.

DETAILED DESCRIPTION OF THE INVENTION

Figure 1:
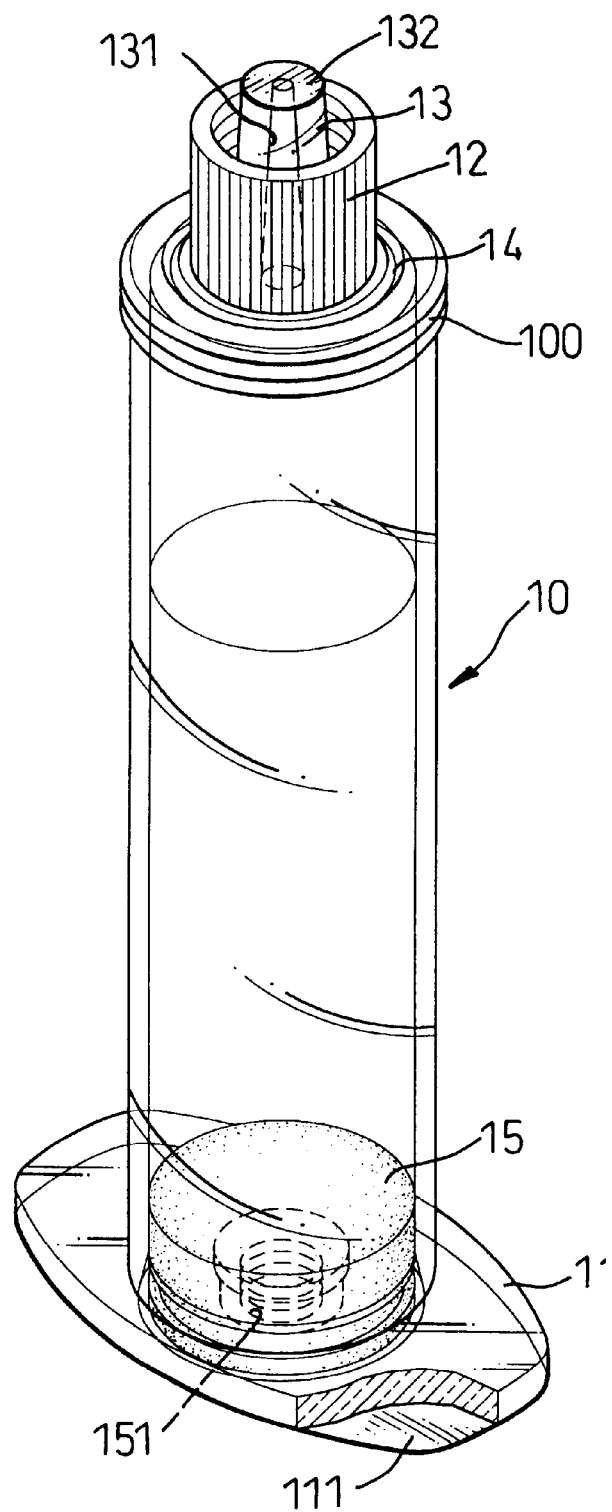
FIG. 1 is a cross-sectional schematic view of a syringe with a barrel used as an ampoule in accordance with the present invention.
Figure 2:
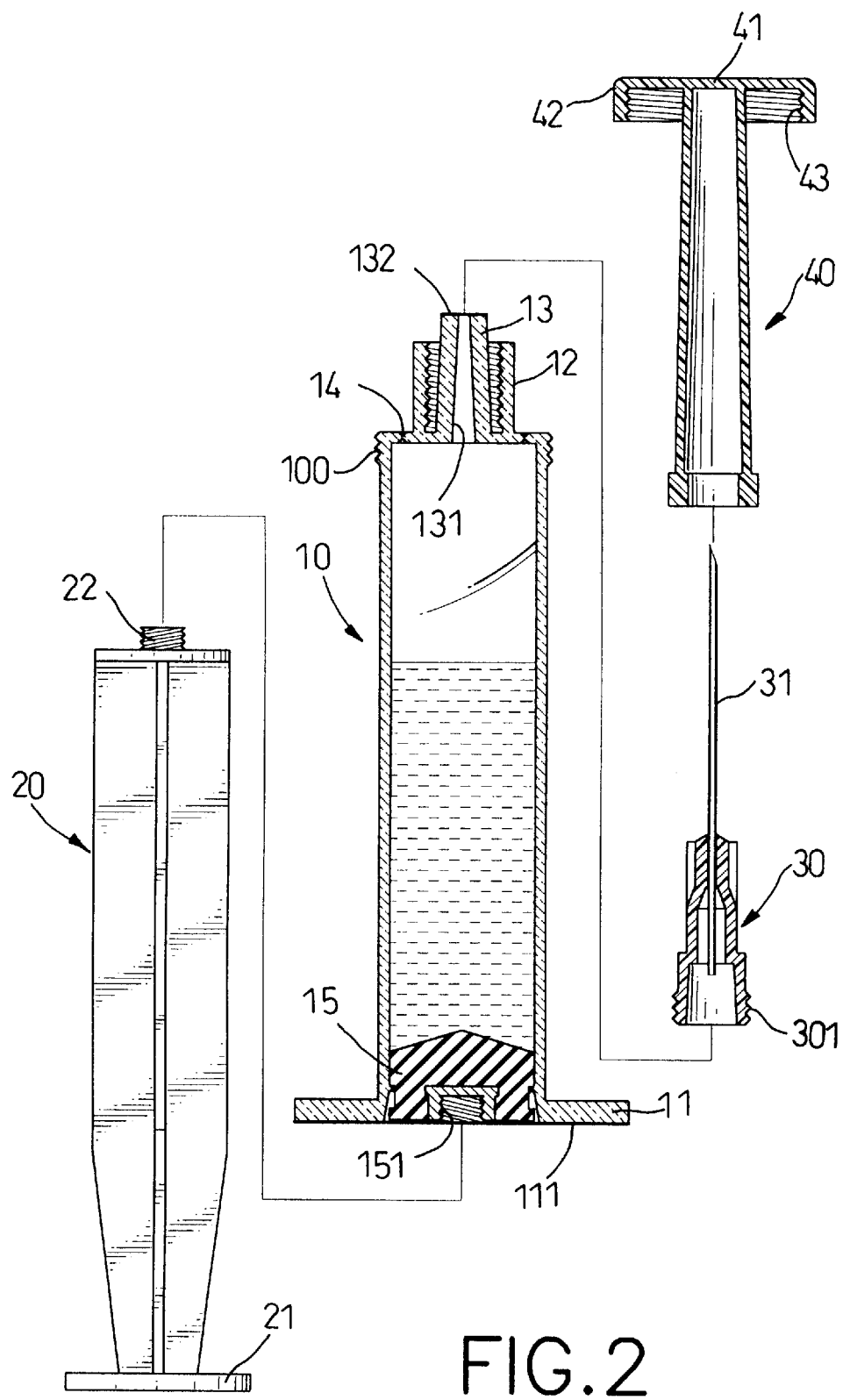
FIG. 2 is a perspective view of the barrel in FIG. 1, showing how the medicine received in the hollow barrel that is contained by two seals.

Referring to the drawings and initially to FIGS. 1 and 2, a syringe in accordance with the present invention comprises a hollow barrel (10) with an open end and a closed end, a plunger (20) slidably received in the hollow barrel (10), a needle hub (30) attached to the closed end of the hollow barrel (10), and a cap (40) enclosing the needle hub (30).

The hollow barrel (10) is pre-filled with medicine (not numbered) in an interior thereof and includes a flange (11) extending out from the open end thereof. A piston (15) is securely and slidably received in the interior of the hollow barrel (10), and in an initial condition is flush with the open end of the hollow barrel (10). A threaded blind hole (151) is centrally defined in the piston (15). A first seal (111) is adhered on the flange (11) to close the open end of the hollow barrel (10) to prevent the medicine from being contaminated. A stub (13) centrally extends out from the closed end of the hollow barrel (10). A through hole (131) is defined in the stub (13) and communicates with the interior of the hollow barrel (10). A second seal (132) is formed on the top of the stub (13) to close the through hole (131) and prevent the medicine in the hollow barrel (10) from being contaminated. An annular flange (12) extends out from the closed end of the hollow barrel (10) and surrounds the stub (13). An interior wall of the annular flange (12) is threaded. An annular groove (14) is defined in the closed end of the hollow barrel (10) and concentrically surrounds the annular flange (12). An exterior wall of the hollow barrel (10) has male thread (100) formed thereon near the closed end of the hollow barrel (10).

The plunger (20) includes a bottom plate (21) extending from a first end thereof and a threaded stub (22) extending out from a second end thereof. The threaded stub (22) is screwed into the threaded hole (151) of the piston (15) whereby a user can push the piston (15) deeper into the hollow barrel (10).

The needle hub (30) is removably attached to the stub (13) and an exterior wall with a threaded portion (301) formed thereon is screwed into the annular flange (12) to secure the needle hub (30) to the closed end of the barrel (10). A needle (31) is securely fitted in the needle hub (30) and has a flat first end received in the threaded portion (301) and a sharp second end. The first end of the needle (31) breaks through the second seal (132) to communicate with the through hole (131) of the stub (13) after the needle hub (30) is attached to the stub (13).

The cap (40) includes an open end and a closed end. The open end of the cap (40) is attached to and partially receives the needle hub (30) to receive the needle (31). The closed end of the cap (40) encloses the second end of the needle (31) to prevent a user from accidentally being pricked by the needle (31). The closed end of the cap (40) has a top plate (41) radially extending out therefrom. An apron (42) extends from an outer periphery of the top plate (41) towards the hollow barrel (10). The apron (42) has an interior wall forming a female thread (43) corresponding to and screwed on the male thread (100) of the hollow barrel (10) after use of the syringe.

Figure 3:
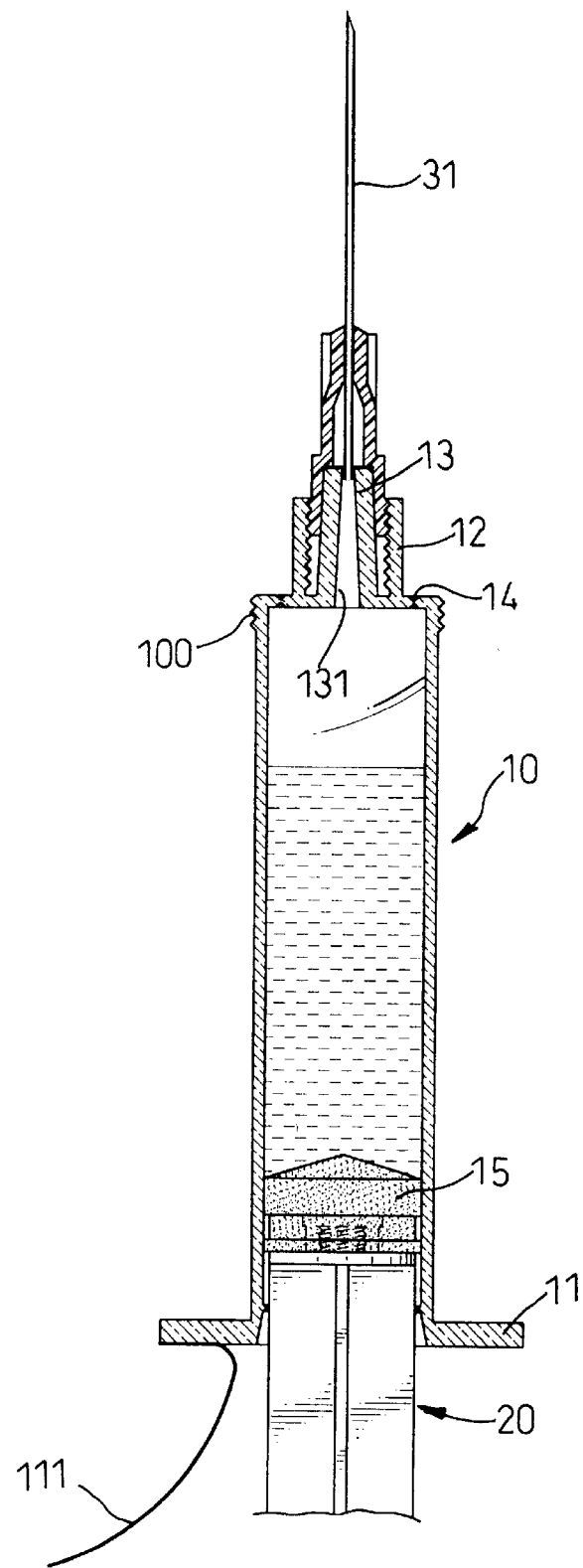
FIG. 3 is an operational view of the syringe with a barrel used as an ampoule in FIG. 1.

When using the syringe, referring to FIGS. 2 and 3, the first seal (111) is taken away from the flange (11) of the hollow barrel (10) and the threaded stub (22) of the plunger (20) is screwed into the threaded hole (151) and secured on the piston (15). The needle hub (30) is attached to the stub (13) of the hollow barrel (10) and the threaded portion (301) is screwed into the threaded interior wall of the annular flange (12). At the same time, the first end of the needle (31) breaks through the second seal (132) to insert into the through hole (131) and communicate with the interior of the hollow barrel (10), and thus further communicate with the medicine therein. The syringe is now ready for application, whereby the cap (40) is removed from the needle hub (30) such that the second end of the needle (31) is exposed ready for penetration of a patient's skin. Once that penetration is achieved, the piston (15) combined with the plunger (20) is pushed into the interior of the hollow barrel (10) whereby the medicine is expelled from the interior of the barrel into the patient via the needle (31).

Figure 4:
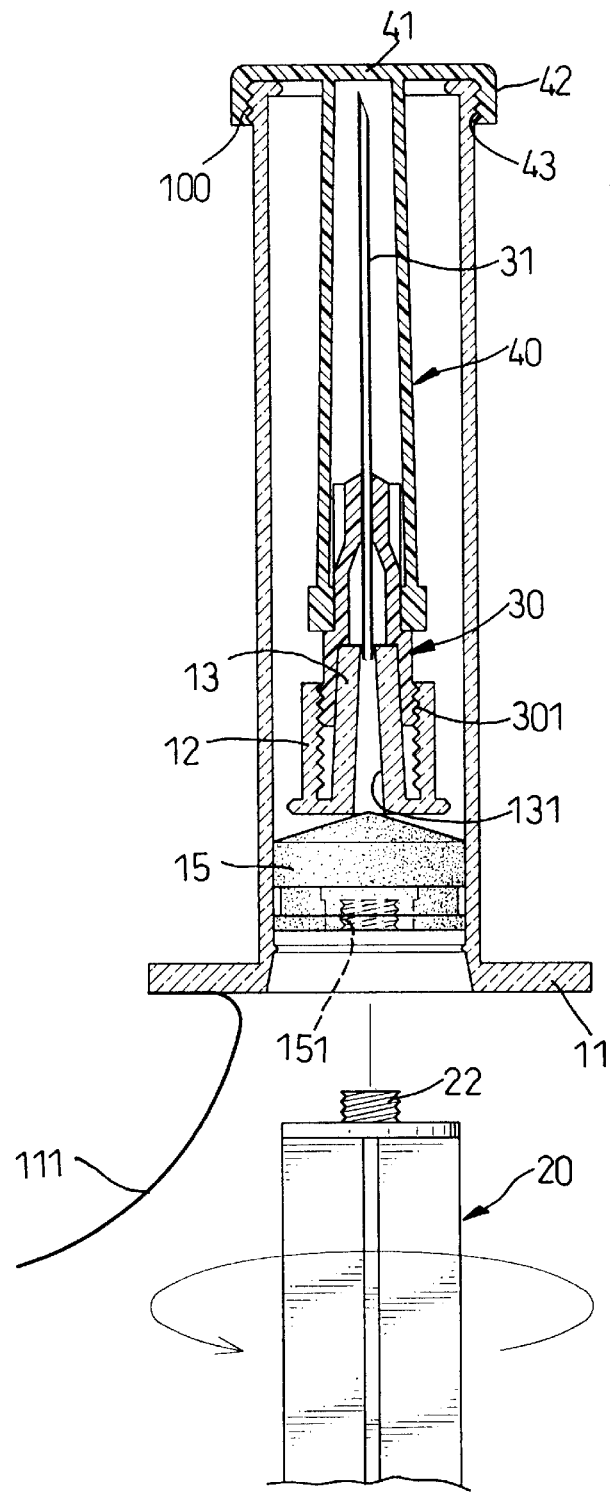
FIG. 4 is a cross-sectional view of the syringe in FIG. 1, showing the used needle stored in the hollow barrel.
Figure 5:
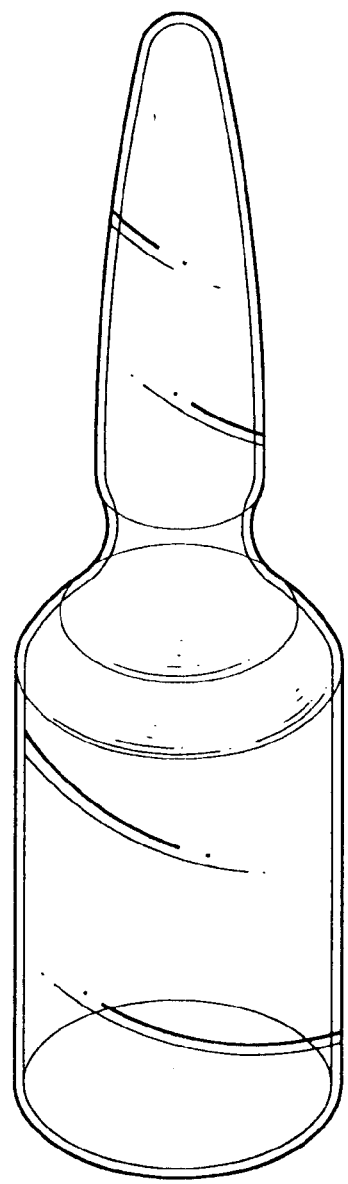
FIG. 5 is a perspective view of an ampoule in accordance with the prior art.

Referring to FIG. 4, once the syringe has been used, the cap (40) is re-attached to the needle hub (30). Then, the user applies force to the annular flange (12) whereby it separates from the hollow barrel (10). The separation is easily achieved because the annular groove (14) formed in the closed end of the hollow barrel (10) provides an easy fracture point. Then, the annular flange (12), the stub (13), the needle hub (30) and the cap (40) are all received in the hollow barrel (10). Last, the female thread (43) of the apron (42) is screwed on the male thread (100) of the hollow barrel (10) to finish the cycle of using the syringe. The plunger (20) can be detached from the piston (15) for subsequent use or be thrown out with the syringe.

As described above, the syringe with a barrel used as an ampoule in accordance with the present invention has several advantages, which are as follow:

1. No need for a separate ampoule means the syringe is safe and convenient.

2. The medicine in the hollow barrel is always isolated and does not contact the air until the needle breaks through the second seal. Extraction of the medicine from an ampoule into the hollow barrel is unnecessary for the syringe in accordance with the present invention.

3. The cost of environmental protection becomes lower. The volume of the garbage is smaller because the ampoule has become redundant and the plunger can be detached for subsequent use.

4. The needle is received and enclosed in the hollow barrel after use and this can prevent the needle from pricking the medical worker or scavengers in garbage sites, whereby the safety of the public is promoted.

Although the invention has been explained in relation to its preferred embodiment, it is to be understood that many other possible modifications and variations can be made without departing from the spirit and scope of the invention as hereinafter claimed.

What is claimed is:

1. A syringe comprising:
   a hollow barrel pre-filled with medicine therein and including an open end and a closed end, a flange extending out from said open end and a piston securely and slidably received in said hollow barrel, and the piston having a pre-use position flush with said open end of said hollow barrel, a first seal adhered on said flange to close said open end of said hollow barrel, a stub centrally extending out from said closed end of said hollow barrel and having a through hole defined to communicate with an interior periphery of said hollow barrel, a second seal formed on a top of said stub to close said through hole, an annular groove defined in said closed end of said hollow barrel and surrounding said annular flange;
   a plunger including a first end removably attached to said piston after said first seal is removed and a second end having a bottom plate radially extending out therefrom;
   a needle hub attached to said stub, a needle securely inserted into said needle hub and penetrating said second seal to communicate with said through hole of said stub after said needle hub is attached to said stub; and
   a cap attached to said needle hub and including an open end and a closed end, said open end of said cap attached to and partially receiving said needle hub to receive said needle therein, said closed end of said cap having a top plate radially extending out therefrom, an apron extending from said periphery of said top plate towards said hollow barrel and mounted on said close end of said hollow barrel.

2. The syringe with a barrel used as an ampoule as claimed in claim 1, wherein said piston includes a threaded hole centrally defined therein and said first end of said plunger has a threaded stub centrally extending therefrom, said threaded stub screwed into said threaded hole of said piston.

3. The syringe with a barrel used as an ampoule as claimed in claim 2, wherein said hollow barrel includes an annular flange extending out from said closed end thereof and between said annular groove and said stub, said annular flange having a interior wall with a thread, said needle hub having a threaded portion formed to screw into said interior wall of said annular flange.

4. The syringe with a barrel used as an ampoule as claimed in claim 3, wherein said hollow barrel includes a male thread formed near said closed end thereof and said apron of said cap has an interior wall with a female thread screwed on said male thread of said hollow barrel.

5. The syringe with a barrel used as an ampoule as claimed in claim 1, wherein said hollow barrel includes an annular flange extending out from said closed end thereof and between said annular groove and said stub, said annular flange having a interior wall with a thread, and said needle hub having a threaded portion formed to screw into said interior wall of said annular flange.

6. The syringe with a barrel used as an ampoule as claimed in claim 5, wherein said hollow barrel includes a male thread formed near said closed end thereof and said apron of said cap has an interior wall with a female thread screwed on said male thread of said hollow barrel.

* * * * *